United States Patent
Christophers et al.

(10) Patent No.: US 6,255,279 B1
(45) Date of Patent: Jul. 3, 2001

(54) COSMETIC PREPARATIONS CONTAINING VERTEBRATE PROTEINS AND HAVING ANTIBACTERIAL, ANTIMYCOTICAL AND ANTIVIRAL ACTION

(75) Inventors: Enno Christophers, Kiel; Udo Hoppe, Hamburg; Jens-M Schröder, Blumenthal; Florian Wolf, Hamburg, all of (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/091,055

(22) PCT Filed: Dec. 4, 1996

(86) PCT No.: PCT/EP96/05405

§ 371 Date: Mar. 15, 1999

§ 102(e) Date: Mar. 15, 1999

(87) PCT Pub. No.: WO97/22624

PCT Pub. Date: Jun. 26, 1997

(30) Foreign Application Priority Data

Dec. 16, 1995 (DE) ................................ 195 47 162
Jul. 19, 1996 (DE) ................................ 196 29 119

(51) Int. Cl.⁷ .............. A61K 7/06; A61K 7/48; A61K 38/17; C07K 14/46
(52) U.S. Cl. .................. 514/2; 424/47; 424/65; 424/70.14; 424/401; 514/12; 514/13; 514/14; 514/15; 514/16; 514/21; 530/324; 530/325; 530/326; 530/327; 530/328; 530/329
(58) Field of Search ................... 424/47, 65, 69, 424/70.14, 76.8, 401; 514/2, 8, 12, 13, 14, 15, 16, 17, 21; 530/300, 324, 325, 326, 327, 328, 329, 330

(56) References Cited

U.S. PATENT DOCUMENTS 5,633,149 * 5/1997 Guegler et al. ............... 435/69.5

OTHER PUBLICATIONS

Wagner–Huber et al. The primary structure of the antenna . . . Eur. J. Biochem. vol. 205, pp. 917–925, 1992.*

* cited by examiner

Primary Examiner—Jeffrey E. Russel
(74) Attorney, Agent, or Firm—Norris McLaughlin & Marcus

(57) ABSTRACT

A peptide which is a monomer, homodimer, heterodimer, homotrimer, heterotrimer, homotetramer or heterotetramer, and is based on the following amino acid sequence:

```
Gly Ile Gly Asp Pro Val Thr Xaa Leu Lys
1             5                    10

Ser Gly Ala Ile Xaa His Pro Val Phe Xaa
              15                   20

Pro Arg Arg Tyr Lys Gln Ile Gly Gly Xaa
              25                   30

Gly Leu Pro Xaa Thr Lys Xaa Xaa Xaa Xaa
              35                   40
``` which has been designated SEQ ID NO.: 1, or a variant of said amino acid sequence, as a homomonomer or heteromonomer. In the forgoing amino acid sequence, each Xaa independently represents an amino acid selected from the group consisting of essential and non-essential amino acids. The peptides have activity against bacteria, mycota, and viruses, and are useful in cosmetic and pharmaceutical compositions against such microorganisms when topically applied to a person.

8 Claims, No Drawings

COSMETIC PREPARATIONS CONTAINING VERTEBRATE PROTEINS AND HAVING ANTIBACTERIAL, ANTIMYCOTICAL AND ANTIVIRAL ACTION

This application is a 371 PCT/EP96/05405 filed on Dec. 4, 1996.

The present invention relates to the use of certain vertebrate proteins as substances active against bacteria, Mycota and viruses. In particular embodiments, the present invention relates to cosmetic and dermatological preparations comprising such substances.

The healthy warm-blooded body, in particular the healthy human skin, is populated by a multiplicity of non-pathogenic microorganisms. This so-called microflora of the skin is not only harmless, it is an important protection for defence against opportunistic or pathogenic microorganisms.

Bacteria belong to the prokaryotic single-cell organisms. They can be differentiated roughly according to their shape (sphere, cylinder, curved cylinder) and according to the construction of their cell wall (gram-positive, gram-negative). Finer subdivisions also take into account the physiology of the organisms. Thus aerobic, anaerobic and optionally anaerobic bacteria exist. Some bacteria are of medical importance by virtue of their property as pathogenic microorganisms, others in turn are completely harmless.

Substances active against bacteria have been known for some time. The term "antibiotic", for example, which is not applicable to all antimicrobially active substances, can be dated to the year 1941, although the first discoveries regarding penicillin had already been made in the year 1929. Antibiotics in the present sense are not suitable for all medicinal applications, even not at all for cosmetic applications, as often the metabolic functions of the warm-blooded body, i.e., for example, of the ill patient, are also adversely affected on administration in any manner.

An object of the present invention was thus to enrich the prior art in this respect, thus in particular to make substances available which are active against gram-positive and/or gram-negative bacteria without the administration of the substances being associated with an unjustifiable adverse effect on the health of the user.

Gram-negative microorganisms are, for example, *Escherichia coli,* Pseudomonas species and also Enterobacteriaceae, such as, for example *Citrobacter freundii.*

Gram-positive microorganisms also play a part in cosmetics and dermatology. In the case of bad skin, for example, besides other influences bacterial secondary infections are of aetiological importance. One of the most important microorganisms which is associated with bad skin is Propionibacterium acnes.

Bad skin and/or comedones adversely affect the well-being of the person affected, however, even in mild cases. As virtually every adolescent is affected by bad skin, in the case of many persons there is a need to remedy this condition.

A particular object of the present invention was thus to find a substance or substance combination active against bad skin or Propionibacterium acnes.

The present invention relates in a further embodiment to cosmetic deodorants. Such formulations are used to eliminate body odour, which is formed when fresh perspiration, which is odourless per se, is decomposed by microorganisms. The customary cosmetic deodorants are based on different active principles.

Both liquid deodorants, for example aerosol sprays, roll-ons and the like and solid preparations, for example deodorant sticks, powders, powder sprays, intimate cleansers etc. are known and customary.

In so-called antiperspirants, the formation of perspiration can be suppressed by astringents—mainly aluminium salts such as aluminium hydroxychloride (aluminium chlorohydrate). Apart from the denaturation of the skin proteins, the substances used for this purpose, however, depending on their dose, intervene drastically in the heat balance of the axillary region and should at best be used in exceptional cases.

By the use of antimicrobial substances in cosmetic deodorants, the bacterial flora on the skin can be reduced. In this process in the ideal case only the odour-causing micro-organisms should effectively be reduced. In practice, however, it has turned out that the entire microflora of the skin can be adversely affected. The flow of perspiration itself is not affected by this means; in the ideal case only the microbial decomposition of the perspiration is temporarily stopped.

The combination of astringents with antimicrobially active substances in one and the same composition is also customary. The disadvantages of the two classes of active compound cannot be completely eliminated in this way, however.

Finally, body odour can also be masked by perfumes, a method which is least satisfactory for the aesthetic needs of the consumer, as the mixture of body odour and perfume fragrance smells rather unpleasant.

However, most cosmetic deodorants, and also most cosmetics altogether, are perfumed, even if they comprise deodorizing active ingredients. Perfuming can also be used to increase the consumer acceptance of a cosmetic product or to give a product a certain flair.

The perfuming of active ingredient-containing cosmetic compositions, in particular cosmetic deodorants, however, is often problematical, because active ingredients and perfume constituents occasionally react with one another and can render each other inactive.

Deodorants should fulfil the following conditions:
1) They should cause reliable deodorization.
2) The natural biological processes of the skin must not be adversely affected by the deodorants.
3) The deodorants must be harmless on overdosage or other unintended use.
4) They should not concentrate on the skin after repeated use.
5) They should be capable of good incorporation in customary cosmetic formulations.

A further object of the present invention was thus to develop cosmetic deodorants which do not have the disadvantages of the prior art. In particular, the deodorants should largely protect the microflora of the skin, but selectively reduce the number of microorganisms which are responsible for body odour.

It was furthermore an object of the invention to develop cosmetic deodorants which are distinguished by good skin compatibility. In no case should the deodorizing active principles concentrate on the skin.

A further object of the invention was to develop cosmetic deodorants which harmonize with as large a number as possible of customary cosmetic auxiliaries and additives, in particular with the perfume constituents important especially in deodorizing or antiperspirant formulations.

Yet a further object of the invention was to make available cosmetic deodorants which are active over a relatively long period of time, namely in the order of magnitude of at least half a day, without their action noticeably decreasing.

Finally, an object of the present invention was to develop deodorizing cosmetic principles which can be incorporated as universally as possible into the widest range of administration forms of cosmetic deodorants without being fixed to one or a few specific administration forms.

Fungi [fungus=Latin], Mycota [μνκηζ=Greek] or mycobionts, as opposed to the bacteria, belong to the eukaryotes. Eukaryotes are organisms whose cells (eucytes), as opposed to those of the so-called prokaryotes (procytes), have a cell nucleus demarcated by a nuclear membrane from the remaining cytoplasm. The cell core contains the genetic information stored in chromosomes.

Representatives of the mycobionts include, for example, yeasts (Protoascomycetes), mold fungi (Plecto-mycetes), mildew (Pyrenomycetes), downy mildew (Phyco-mycetes) and club fungi (Basidiomycetes).

Fungi, not even the Basidiomycetes, are not plant organisms, but like these have a cell wall, cell sap-filled vacuoles and a microscopically readily visible plasma flow. They contain no photosynthetic pigments and are C-heterotrophic. They grow under aerobic conditions and obtain energy by oxidation of organic substances. Some representatives, for example yeasts, however, are facultative anaerobes and capable of obtaining energy by fermentation processes.

Dermatomycoses are diseases in which certain fungal species, in particular Dermatophytes, penetrate into the skin and hair follicles. The symptoms of dermatomycoses are, for example, vesicles, exfoliation, rhagades and erosion, mostly associated with itching or allergic eczema.

Dermatomycoses can essentially be subdivided into the following four groups: dermatophytoses (e.g. epidermophytosis, favus, microsporosis, trichophytosis), yeast mycoses (e.g. pityriasis and other Pityrosporum-related mycoses, Candida infections, blastomycosis, Busse-Buschke disease, torulosis, piedra alba, torulopsidosis, trichosporosis), hyphomycoses (e.g. aspergillosis, cephalosporidosis, phycomycosis and scopulariopsidosis), systemic mycoses (e.g. chromomycosis, coccidiomycoses, histoplasmoses).

The pathogenic and facultatively pathogenic microorganisms include, for example from the yeasts group, Candida species (e.g. *Candida albicans*) and those of the Pityrosporum family. Pityrosporum species, in particular *Pityrosporum ovale*, are to be held responsible for skin disorders such as *Pityriasis versicolour*, seborrhoea in the forms seborrhoea oleosa and seborrhoea sicca, which are manifested especially as seborrhoea capitis (=dandruff), seborrhoeic eczema and *Pityrosporum folliculitis*. An involvement of *Pityrosporum ovale* in the formation of psoriasis is being discussed among experts.

All areas of the human skin can be attacked by dermatomycoses. Dermatophytoses attack skin, hair and nails almost exclusively. Saccharomycoses can also attack mucous membranes and internal organs; systemic mycoses regularly extend over entire organ systems.

Those body areas are particularly frequently affected on which dampness and heat can build up as a result of clothing, jewelry or footwear. Pedal mycosis thus belongs to the best known and most widespread dermatomycoses. Furthermore, fungal disorders of the fingernail and toenail regions are particularly unpleasant.

Superinfections of the skin by fungi and bacteria furthermore are not rare.

In the case of existing primary infection, i.e. new infection of the normal microorganism population of the skin occurring with high microorganism counts of one or more often physiological pathogens, for example Staphylococci, but often also of non-physiological pathogens, for example *Candida albicans*, a "superinfection" of the attacked skin can occur with coincidence of unfavourable effects. The normal microflora of the skin (or of another body organ) is in this case utterly overgrown by the secondary pathogen.

Such superinfections can be manifested, depending on the microorganism concerned, in unpleasant skin symptoms (itching, unsightly external appearance) in favourably progressing cases. In unfavourably progressing cases, however, they can lead to large-area destruction of the skin and in the worst case even culminate in the death of the patient.

Superinfections of the type first described are, for example, frequently occurring secondary disorders in the full AIDS syndrome. Pathogenic microorganisms which are harmless per se—in any case at low microorganism densities—but also markedly pathogenic under certain circumstances in this way overgrow the healthy skin flora. In the case of AIDS, however, other body organs are also affected by superinfections.

Superinfections of this type are also observed in a multiplicity of dermatological disorders, e.g. atopic eczema, neurodermatitis, acne, seborrhoeic dermatitis or psoriasis. Many medicinal and therapeutic measures, e.g. the radio- or chemotherapy of cancers, drug-induced immunosuppression caused as a side effect or even systemic antibiotic treatment, as well as external chemical or physical effects (e.g. environmental pollution, smog), promote the occurrence of superinfections of the external and internal organs, in particular of the skin and of the mucous membranes.

Although in the individual case it is possible without difficulty to control superinfections with antibiotics, such substances, however, usually have the disadvantage of unpleasant side effects. Patients are often allergic, for example, to penicillins, which is why a relevant treatment would be avoided in such a case.

Topically administered antibiotics further have the disadvantage that they not only free the skin flora from the secondary pathogen, but also severely adversely affect the physiological skin flora in itself and the natural healing process is again slowed down in this way.

The object of the present invention was to eliminate the disadvantages of the prior art and to make available substances and preparations comprising such substances by whose use superinfections can be healed, the physiological skin flora suffering no noticeable losses.

In contrast to the prokaryotic and eukaryotic cellular organisms, viruses [virus=Latin poison] are biological structures which need a host cell for biosynthesis. Extracellular viruses (also called "virions") consist of a single- or double-stranded nucleic acid sequence (DNA or RNA) and a protein coat (called a capsid), optionally surrounded by an additional lipid-containing envelope. The nucleic acid and capsid as a whole is also called a nucleocapsid. The classification of the viruses was carried out classically according to clinical criteria, but today is usually carried out according to their structure, their morphology, but in particular according to the nucleic acid sequence.

Medically important virus genera are, for example, influenza viruses (Orthomyxoviridae family), lyssaviruses (e.g. rabies, rhabdoviruses family), enteroviruses (e.g. hepatitis A, Picornaviridae family), hepadnaviruses (e.g. hepatitis B, Hepadnaviridae family).

Virucides, i.e. virus-destroying substances, in the real sense do not exist, as viruses do not have their own metabolism. For this reason, it was also discussed whether viruses should be classified as organisms. Pharmacological interventions without damage to the unaffected cells is difficult in any case. Possible mechanisms of action in the battle against the viruses are primarily the disruption of their replication, e.g. by blocking the enzymes important for replication, which are present in the host cell. The release of the viral nucleic acids into the host cell can further be prevented. In the context of the disclosure presented hereby, terms such as "antiviral" or "active against viruses", "virucidal" or the like are understood as meaning the property of a substance of protecting a single- or multi-celled organism from the harmful consequences of a virus infection, be it prophylactically or therapeutically, in spite of what the actual mechanism of action of the substance in the individual case may be.

The prior art, however, lacks substances active against viruses, which moreover do not damage the host organism or only damage it to a justifiable extent.

An object of the present invention was thus to remedy this unsatisfactory situation, i.e. to find substances which effectively protect a single- or multi-celled organism from the harmful consequences of a virus infection, be it prophylactically or therapeutically.

It has surprisingly been found, and therein lies the achievement of this object, that (1) monomeric or homo- or heterodimeric or homo- or heterotrimeric or homo- or heterotetrameric peptides, these peptides being based as homo- or heteromonomer on a structure or a structural motif

```
                                         (SEQ ID NO:1)
   1        10        20        30        40
   GIGDPVTXLKSGAIXHPVFXPRRYKQIGGXGLPXTKXXXX,
```

X being selected at will from the group consisting of the essential and non-essential amino acids, (2) or, in the monomeric or homo- or heterodimeric or homo- or heterotrimeric or homo- or heterotetrameric peptides, structures such as the abovementioned being present with the difference that up to any five desired amino acids are absent, up to any five desired amino acids are replaced by up to any five other desired amino acids, or in up to any five desired sites up to any five further desired amino acids are present, (3) or, in the monomeric or homo- or heterodimeric or homo- or heterotrimeric or homo- or heterotetrameric peptides, structures such as the abovementioned being present with the difference that up to 17 amino acids are deleted from and/or added to the C terminus and/or the N terminus, (4) or, in monomeric or homo-/hetero-di-, -tri- or -tetrameric peptides or proteins having a molecular weight between 10 and 100 kDaltons, amino acid sequences indicated under items (1), (2) and (3) occurring as structural motifs present singly or recurring several times, remedy the disadvantages of the prior art.

Particular embodiments of the present invention are regarded as being cosmetic or pharmaceutical preparations which are distinguished by an efficacious content of (1) one or more monomeric or homo- or heterodimeric or homo- or heterotrimeric or homo- or heterotetrameric peptides, these peptides being based as homo- or heteromonomer on a structure

```
                                         (SEQ ID NO:1)
   1        10        20        30        40
   GIGDPVTXLKSGAIXHPVFXPRRYKQIGGXGLPXTKXXXX,
```

X being selected at will from the group consisting of the essential and non-essential amino acids, (2) or, in the monomeric or homo- or heterodimeric or homo- or heterotrimeric or homo- or heterotetrameric peptides, structures such as the abovementioned being present with the difference that up to any five desired amino acids are absent, up to any five desired amino acids are replaced by up to any five other desired amino acids, or in up to any five desired sites up to any five further desired amino acids are present, (3) or, in the monomeric or homo- or heterodimeric or homo- or heterotrimeric or homo- or heterotetrameric peptides, structures such as the abovementioned being present with the difference that up to 17 amino acids are deleted from and/or added to the C terminus and/or the N terminus, (4) or, in monomeric or homo-/hetero-di-, -tri- or -tetrameric peptides or proteins having a molecular weight between 10 and 100 kDaltons, amino acid sequences indicated under items (1), (2) and (3) occurring as structural motifs present singly or recurring several times.

Table 1 juxtaposes the essential amino acids with their corresponding three- and one-letter codes. For the sake of simplicity, we use the one-letter code for the characterization of the structures according to the invention.

TABLE 1

| Three- and one-letter codes for amino acids | | |
|---|---|---|
| Amino acid | | |
| L-alanine | Ala | A |
| L-valine | Val | V |
| L-leucine | Leu | L |
| L-isoleucine | Ile | I |
| L-proline | Pro | P |
| L-tryptophan | Typ | W |
| L-phenylalanine | Phe | F |
| L-methionine | Met | M |
| glycine | Gly | G |
| L-serine | Ser | S |
| L-tyrosine | Tyr | Y |
| L-threonine | Thr | T |
| L-cysteine | Cys | C |
| L-asparagine | Asn | N |
| L-glutamine | Gln | Q |
| L-aspartic acid | Asp | D |
| L-glutamic acid | Glu | E |
| L-lysine | Lys | K |
| L-arginine | Arg | R |
| L-histidine | His | H |

Here, L-selenocysteine can replace L-cysteine and L-selenomethionine can replace L-methionine. Moreover, individual positions, several positions or alternatively all positions can also be replaced by the corresponding stereoisomers having the D configuration.

(a) A very preferred peptide or peptides is/are regarded as being monomeric or homo- or heterodimeric or homo- or heterotrimeric or homo- or heterotetrameric peptides, these peptides being based as homo- or heteromonomer on a structure or a structural motif

```
                                    (SEQ ID NO:2)
    1         10        20        30        40
    GIGDPVTCLKSGAICHPVFCPRRYKQIGTCGLPGTTCCKKP
```

An advantageous embodiment is regarded as being such peptides or preparations comprising such peptides which are obtainable from the skin of vertebrates, for example by extraction processes. It is clear to the person skilled in the art here that such peptides are also synthetically accessible in other ways, for example by chemical synthesis or biotechnological processes.

The use of such active ingredients as antibacterial, antimycotic or antiviral active ingredients is also novel. The use of the active ingredients according to the invention as active ingredients active against gram-positive bacteria is very particularly advantageous.

It has surprisingly emerged that the active ingredients used according to the invention prevent the growth of gram-positive and gram-negative bacteria, mycobionts and viruses.

In particular, the active ingredients used according to the invention are capable of preventing the growth of yeasts, in particular of the Pityrosporum species, namely *Pityrosporum ovale*.

It has further emerged that the active ingredients used according to the invention prevent the formation of seborrhoeic symptoms, in particular dandruff, and also eliminate seborrhoeic symptoms already present, in particular dandruff.

The active ingredients used according to the invention are moreover suitable for use as deodorizing active ingredient in cosmetic deodorants and also against bad skin, mild forms of acne or Propionibacterium acnes.

The active ingredients according to the invention have likewise proved to be particularly effective against Streptococci.

Finally, it has emerged that the active ingredients used according to the invention can prevent the decay of organic substances, in particular cosmetic and dermatological preparations, due to attack with gram-positive and gram-negative bacteria, mycobionts and viruses, if they are added to these preparations.

According to the invention, a process for the control of mycobionts is thus also characterized in that the active ingredients used according to the invention, if appropriate in a suitable cosmetic or dermatological carrier, are brought into contact with the area contaminated by mycobionts, and a process for the protection of organic products from attack with mycobionts is characterized in that the active ingredients used according to the invention are added to these organic products in an effective amount.

The prior art consequently did not provide the slightest indication of the use according to the invention as an antimycotic active principle.

It was furthermore surprising that the active ingredients used according to the invention are particularly highly effective against the microorganism *Pityrosporum ovale* and related microorganisms responsible for the formation of dandruff. A preferred embodiment of the present invention are therefore formulations to be used against dandruff, for example anti-dandruff shampoos.

According to the invention, the active ingredients are preferably employed in cosmetic or dermatological compositions, a content of 0.0005–50.0% by weight, in particular 0.01–20.0% by weight, based on the total weight of the composition, being preferred. Advantageously, the compositions contain 0.02–10.0% by weight, particularly preferably 0.02–5.0% by weight of the active ingredients used according to the invention, very particularly advantageously 0.5–3.0% by weight, in each case based on the total weight of the composition.

The active ingredients used according to the invention can be incorporated without difficulties into conventional cosmetic or dermatological formulations, advantageously in pump sprays, aerosol sprays, creams, ointments, tinctures, lotions, nail-care products (e.g. nail varnishes, nail varnish removers, nail balms) and the like.

It is also possible and optionally advantageous to combine the active ingredients used according to the invention with other active ingredients, for example with other antimicrobially, antimycotically or antivirally active substances.

It is advantageous to buffer the compositions according to the invention. A pH range of 3.5–7.5 is advantageous. It is particularly favourable to select the pH in a range of 4.0–6.5.

The cosmetic and/or dermatological formulations according to the invention can be made up in the customary manner and used for the treatment of the skin and/or of the hair in the sense of a dermatological treatment or of a treatment in the sense of medicated cosmetics. However, they can also be employed in decorative cosmetics in make-up products.

For use, the cosmetic and/or dermatological formulations according to the invention are applied to the skin and/or the hair in adequate amount in the manner customary for cosmetics and dermatological agents.

Those cosmetic and dermatological preparations which are present in the form of a sunscreen composition are advantageous. Advantageously, these additionally contain at least one UVA filter and/or at least one UVB filter and/or at least one inorganic pigment.

Cosmetic preparations according to the invention for the protection of the skin from UV rays can be present in various forms, such as are customarily employed for this type of preparations. They can thus be, for example, a solution, an emulsion of the water-in-oil (W/O) type or of the oil-in-water (O/W) type, or a multiple emulsion, for example of the water-in-oil-in-water (W/O/W) type, a gel, a hydrodispersion, a solid stick or alternatively an aerosol.

The cosmetic preparations according to the invention can contain cosmetic auxiliaries such as are customarily used in such preparations, e.g. preservatives, bactericides, antioxidants, perfumes, agents for preventing foaming, colorants, pigments which have a colouring action, thickeners, surface-active substances, emulsifiers, emollient substances, moisturizing and/or moisture-retaining substances, fats, oils, waxes or other customary constituents of a cosmetic formulation such as alcohols, polyols, polymers, foam stabilizers, electro-lytes, organic solvents or silicone derivatives.

If the cosmetic or dermatological preparation is a solution or lotion, the solvents used can be:

water or aqueous solutions;

oils, such as triglycerides of capric or of caprylic acid, but preferably castor oil;

fats, waxes and other natural and synthetic fatty materials, preferably esters of fatty acids with alcohols of low C number, e.g. with isopropanol, propylene glycol or glycerol, or esters of fatty alcohols with alkanoic acids of low C number or with fatty acids;

alcohols, diols or polyols of low C number, and also their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the abovementioned solvents are used. In the case of alcoholic solvents, water can be a further constituent.

According to the invention, all antioxidants suitable or customary for cosmetic and/or dermatological uses can be used as favourable antioxidants.

Advantageously, the antioxidants are selected from the group consisting of amino acids (e.g. glycine, histidine, tyrosine, tryptophan) and their derivatives, imidazoles (e.g. urocanic acid) and their derivatives, peptides such as D,L-carnosine, D-carnosine, L-carnosine and their derivatives (e.g. anserine), carotenoids, carotenes (e.g. α-carotene, β-carotene, lycopene) and their derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulphoximine compounds (e.g. buthionine sulphoximines, homocysteine sulphoximine, buthionine sulphones, penta-, hexa- or heptathioninesulphoxime) in very low tolerable doses (e.g. pmol to μmol/kg), further (metal) chelators (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg-ascorbyl phosphate, ascorbyl acetate), tocopherols and derivatives (e.g. vitamin E acetate), vitamin A and derivatives (vitamin A palmitate) and coniferyl benzoate from benzoin, rutic acid and its derivatives, ferulic acid and its derivatives, butylhydroxytoluene, butylhydroxyanisole, nordihydroguaiaretic acid, trihydroxybutyrophenone, uric acid and its derivatives, mannose and its derivatives, zinc and its derivatives (e.g. ZnO, $ZnSO_4$), selenium and its derivatives (e.g. selenomethionine), stilbenes and their derivatives (e.g. stilbene oxide, trans-stilbene oxide) and the derivatives suitable according to the invention (salts, esters, ethers, sugars, nucleotides, nucleosides, peptides and lipids) of these said active compounds.

The amount of the antioxidants (one or more compounds) in the preparations is preferably 0.001 to 30% by weight, particularly preferably 0.05–20% by weight, in particular 1–10% by weight, based on the total weight of the preparation.

If vitamin E and/or its derivatives is/are the antioxidant(s), it is advantageous to select its respective concentrations from the range 0.001–10% by weight, based on the total weight of the formulation.

If vitamin A, and/or vitamin derivatives, and/or carotenes or their derivatives is/are the antioxidant(s), it is advantageous to select their respective concentrations from the range 0.001–10% by weight, based on the total weight of the formulation.

Emulsions according to the invention are advantageous and contain, for example, the said fats, oils, waxes and other fatty materials, and also water and an emulsifier, such as is customarily used for such a type of formulation.

Gels according to the invention customarily contain alcohols of low C number, e.g. ethanol, isopropanol, 1,2-propanediol, glycerol and water or an abovementioned oil in the presence of a thickening agent which, in the case of oily-alcoholic gels, is preferably silica or an aluminium silicate, and in the case of aqueous-alcoholic or alcoholic gels is preferably a poly-acrylate.

Solid sticks according to the invention contain, for example, natural or synthetic waxes, fatty alcohols or fatty acid esters. Lip-care sticks and deodorizing sticks ("deodorant sticks") are preferred.

Suitable propellants for cosmetic or dermatological preparations according to the invention which can be sprayed from aerosol containers are the customary known readily volatile, liquefied propellants, e.g. hydrocarbons (propane, butane, isobutane) which can be employed on their own or in a mixture with one another. Compressed air can also be used advantageously.

Of course, the person skilled in the art knows that there are non-toxic propellant gases which would be fundamentally suitable for the present invention, but which nevertheless should be dispensed with because of questionable effects on the environment or other con-comitant circumstances, in particular fluorohydrocarbons (FCs) and chlorofluorohydrocarbons (CFCs).

The preparations according to the invention can preferably moreover contain substances which absorb UV radiation in the UVB range, the total amount of the filter substances being, for example, 0.1% by weight to 30% by weight, preferably 0.5 to 10% by weight, in particular 1 to 6% by weight, based on the total weight of the preparation, in order to make available cosmetic preparations which protect the skin from the entire range of ultraviolet radiation. They can also be used as sunscreen compositions.

The UVB filters can be oil-soluble or water-soluble. Oil-soluble substances which may be mentioned, for example, are:

3-benzylidenecamphor and its derivatives, e.g. 3-(4-methylbenzylidene) camphor, 4-aminobenzoic acid derivatives, preferably 2-ethylhexyl 4-dimethylaminobenzoate, amyl 4-dimethylamino-benzoate;

esters of cinnamic acid, preferably 2-ethylhexyl 4-methoxycinnamates, isopentyl 4-methoxycinnamate;

esters of salicylic acid, preferably 2-ethylhexyl salicylate, 4-isopropylbenzyl salicylate, homo-menthyl salicylate;

derivatives of benzophenone, preferably 2-hydroxy-4-methoxybenzophenone, 2-hydroxy-4-methoxy-4'-methyl-benzophenone, 2,2'-dihydroxy-4-methoxybenzophenone;

esters of benzylidenemalonic acid, preferably di(2-ethylhexyl) 4-methoxybenzylidene malonate;

2,4,6-trianilino-(p-carbo-2'-ethyl-1'-hexyloxy)-1,3,5-triazine

The following are advantageous as water-soluble substances:

2-phenylbenzimidazole-5-sulphonic acid and its salts, e.g. sodium, potassium or triethanolammonium salts, sulphonic acid derivatives of benzophenones, preferably 2-hydroxy-4-methoxybenzophenone-5-sulphonic acid and its salts;

sulphonic acid derivatives of 3-benzylidenecamphor, e.g. 4-(2-oxo-3-bornylidenemethyl)benzenesulphonic acid, 2-methyl-5-(2-oxo-3-bornylidenemethyl)-sulphonic acid and their salts.

The list of the said UVB filters which can be used according to the invention should, of course, be non-limiting.

It can also be advantageous to employ in preparations according to the invention UVA filters which are customarily contained in cosmetic and/or dermatological preparations. Such substances are preferably derivatives of dibenzoylmethane, in particular 1-(4'-tert-butyl-phenyl)-3-(4'-methoxyphenyl)propane-1,3-dione and 1-phenyl-3-(4'-isopropylphenyl)propane-1,3-dione. The invention also relates to preparations which contain these combinations. The same amounts of UVA filter substances can be used which have been mentioned for UVB filter substances.

Cosmetic and/or dermatological preparations according to the invention can also contain inorganic pigments which are customarily used in cosmetics for the protection of the skin from UV rays. These are oxides of titanium, zinc, iron, zirconium, silicon, manganese, aluminium, cerium and mixtures thereof, and also modifications in which the oxides are the active agents. They are particularly preferably pigments based on titanium dioxide. The amounts mentioned for the above combinations can be used.

Cosmetic preparations for the care of the hair are, for example, shampoos, preparations which are used on rinsing the hair before or after shampooing, before or after permanent wave treatment or before or after dyeing or bleaching the hair, preparations for drying or setting the hair, preparations for dyeing or bleaching, a hair-dressing and treatment lotion, a hair lacquer or permanent wave compositions.

The cosmetic preparations contain active ingredients and auxiliaries such as are customarily used for this type of preparations for hair care and hair treatment.

Auxiliaries used are preservatives, surface-active substances, substances for preventing foaming, emulsifiers, thickeners, fats, oils, waxes, organic solvents, bactericides, perfumes, colourants or pigments, whose object is to colour the hair or the preparation itself, electrolytes, preparations against greasing of the hair.

Cosmetic preparations which are a shampoo or a washing, shower or bath preparation preferably contain at least one anionic, non-ionic or amphoteric surface-active substance or mixtures thereof, active ingredients according to the invention and auxiliaries such as are customarily used for this purpose.

Examples of surface-active substances which can advantageously be used according to the invention are conventional soaps, e.g. fatty acid salts of sodium, alkylsulphates, alkyl ether sulphates, alkane-and alkylbenzenesulphonates, sulphoacetates, sulphobetaines, sarcocinates, amidosulphobetaines, sulphosuccinates, sulphosuccinic acid hemiesters, alkyl ether carboxylates, protein-fatty acid condensates, alkylbetaines and amido-betaines, fatty acid alkanolamides, polyglycol ether derivatives.

The surface-active substance can be present in a concentration of between 1% by weight and 50% by weight in the shampoo, or the washing, shower or bath preparation.

If the cosmetic or dermatological preparation is present in the form of a lotion which can be rinsed out and used, for example, before or after bleaching, before or after shampooing, between two shampooing steps or before or after permanent wave treatment, it is in this case, for example, aqueous or aqueous-alcoholic solutions which optionally contain surface-active substances, preferably non-ionic or cationic surface-active substances whose concentration can be between 0.1 and 10% by weight, preferably between 0.2 and 5% by weight. This cosmetic or dermatological preparation can also be an aerosol containing the auxiliaries customarily used for this purpose.

A cosmetic preparation in the form of a lotion which in not rinsed out, in particular a lotion for setting the hair, a lotion which is used when drying the hair, a hairdressing and treatment lotion, is in general an aqueous, alcoholic or aqueous-alcoholic solution and contains at least one cationic, anionic, non-ionic or amphoteric polymer or alternatively mixtures thereof, and active ingredients according to the invention. The amount of the active ingredients according to the invention used is, for example, between 0.1 and 10% by weight, preferably between 0.1 and 3% by weight.

Cosmetic and dermatological preparations for the treatment and care of the hair, which contain the active ingredients used according to the invention, can be present as emulsions which are of the non-ionic or anionic type. Besides water, non-ionic emulsions contain oils or fatty alcohols which, for example, can be polyethoxylated or polypropoxylated, or alternatively mixtures of the two organic components. These emulsions contain optionally cationic surface-active substances.

Cosmetic and dermatological preparations for the treatment and care of the hair can be present as gels which, in addition to active ingredients used according to the invention and solvents customarily used for this purpose, additionally contain organic thickeners, e.g. gum arabic, xanthan gum, sodium alginate, cellulose derivatives, preferably methylcellulose, hydroxymethylcellulose, hydroxyethylcellulose, hydroxypropylcellulose, hydroxypropylmethylcellulose, or inorganic thickeners, e.g. aluminium silicates such as bentonites, or a mixture of polyethylene glycol and polyethylene glycol stearate or distearate. The thickener is contained in the gel, for example, in an amount between 0.1 and 30% by weight, preferably between 0.5 and 15% by weight.

The amount of the active ingredients used according to the invention in a composition intended for the hair is preferably 0.01% by weight to 10% by weight, in particular 0.5% by weight to 5% by weight, based on the total weight of the preparations.

The following examples are intended to illustrate the embodiments of the present invention. The details always relate to % by weight, if other details are not given.

Since peptides according to the invention can be obtained from the skin of vertebrates, inter alia from human skin, the abbreviation "SAP" (=skin antimicrobial peptide) will be used here and below for such peptides.

Procedure for the Isolation of SAP from Human Skin 50 g of scales from the skin of psoriatic subjects were comminuted in 0.1 mol/l citrate buffer, pH 3.0, with the aid of a dispersing apparatus. After addition of 30% by volume of ethanol, the mixture was centrifuged and the clear supernatant was diafiltered against phosphate-buffered saline solution (PBS), pH 7.4, through an Amicon YM-3 filter (cut-off: 3 kDa). After centrifugation, the clear supernatant was added to an affinity column covalently coated with mouse immunoglobulin (HiTRAP, NHS-activated, 1 ml, Pharmacia AB) and the column was washed with 2 ml of PBS.

Bound proteins were eluted first with 10 ml of 2 M sodium chloride solution and then 10 ml of 0.2 M glycine/HCl solution (pH 2.0).

The NaCl eluate and the glycine/HCl eluate were combined and first diafiltered through an Amicon YM-3 filter against 0.1% trifluoroacetic acid in water and then concentrated. The concentrate was then added to a preparative reversed-phase HPLC column (RP-8, 250 mm×12.5 mm, 300–7 C8, Macherey and Nagel) and chromato-graphed using a linear gradient of rising concentrations of acetonitrile in 0.1% trifluoroacetic acid/water. The absorption of the column eluate was measured at 220 nm. Fractions which were eluted using 32–36% acetonitrile were combined and separated further on a Microbore Mono S-HPLC column (Smart Micro-HPLC Apparatus, Pharmacia AB) which had previously been equilibrated with 50 mmol/l of ammonium formate.

Proteins were eluted with the aid of a rising NaCl gradient (maximum: 1 mol/l) in the equilibration buffer. The proteins elutable in the range 0.48 mol/l to 0.55 mol/l were collected and finally subjected to a Microbore RP-18 HPLC separation.

The protein elutable at 39% acetonitrile was collected. An SDS-PAGE analysis with the aid of high-density gels (Pharmacia AB) and the Phast electrophoresis system (Pharmacia AB) showed a broadened band corresponding to 15 kDa after silver staining.

$NH_2$-terminal sequencing experiments by Edman degradation in an amino acid analyzer (Applied Bio-systems) showed a primary structure

```
                                        (SEQ ID NO:2)
1        10        20        30        40
    GIGDPVTCLKSGAICHPVFCPRRYKQIGTCGLPGTTCCKKP
```

EXAMPLE 1

W/O lotion

|  | % by wt. |
|---|---|
| Liquid paraffin | 25.00 |
| Silicone oil | 2.00 |
| Ceresin | 1.50 |
| Wool wax alcohol | 0.50 |
| Glucose sesquiisostearate | 2.50 |
| SAP | 50 mg/l |
| Perfume, preservatives | q.s. |
| Water, completely demineralized | to 100.00 |
| pK: | to 5.5–6.0 |

EXAMPLE 2

O/W cream

|  | % by wt. |
|---|---|
| Vegetable oil | 10.00 |
| Cetyl alcohol | 2.00 |
| Glycerol monostearate | 1.50 |
| PEG 30-glyceryl stearate | 2.00 |
| Glycerol | 3.00 |
| Isopropyl palmitate | 5.00 |
| Carbopol 980 (neutralized) | 0.30 |
| SAP | 50 mg/l |
| Perfume, preservativee | q.s. |
| Water, completely demineralized | to 100.00 |
| pH: | to 5.5–6.0 |

EXAMPLE 3

Lipstick

|  | % by wt. |
|---|---|
| Ceresin | 8.00 |
| Beeswax | 4.00 |
| Carnauba wax | 2.00 |
| Petroleum jelly | 40.00 |
| Hydrogenated castor oil | 4.60 |
| Caprylic/capric triglyceride | 6.00 |
| SAP | 100 mg/l |
| Perfume, preservatives | q.s. |
| Water, completely demineralized | to 100.00 |
| pH: | to 5.5–6.0 |

EXAMPLE 4

Liposome-containing face care gel

|  | % by wt. |
|---|---|
| Lecithin | 6.00 |
| Vegetable oil | 12.50 |
| Hydrolysed collagen | 2.00 |
| Xanthan gum | 1.40 |
| Butylene glycol | 3.00 |
| SAP | 50 mg/l |
| Perfume, preservatives | q.s. |
| Water, completely demineralized | to 100.00 |
| pH: | to 5.5–6.0 |

EXAMPLE 5

Shower preparation with refatting agent

|  | % by wt. |
|---|---|
| Coconut amidodiacetate | 10.00 |
| Sodium lauryl sulphate | 25.00 |
| Potassium cocoyl hydrolysed collagen | 5.00 |
| Macadamia nut oil | 5.00 |
| Sodium chloride | 0.60 |
| SAP | 150 mg/l |
| Perfume, preservatives | q.s. |
| Water, completely demineralized | to 100.00 |
|  | to 5.5–6.0 |

EXAMPLE 6

Syndet soap

|  | % by wt. |
|---|---|
| Sodium lauryl sulphate | 30.00 |
| Sodium sulphosuccinate | 10.00 |
| Potassium cocoyl hydrolysed collagen | 2.00 |
| Dimethicone copolyol | 2.00 |
| Paraffin | 2.00 |
| Maize starch | 10.00 |
| Talc | 10.00 |
| Glycerol | 3.00 |

-continued

Syndet soap

| | % by wt. |
|---|---|
| SAP | 75 mg/l |
| Perfume, preservatives | q.s. |
| Water, completely demineralized | to 100.00 |
| pH: | to 5.5–6.0 |

EXAMPLE 7

Medicated shampoo

| | % by wt. |
|---|---|
| Sodium lauryl sulphate | 34.00 |
| Disodium lauryl sulphosuccinate | 6.00 |
| cocoamidopropylbetaine | 10.00 |
| Glycol distearate | 5.00 |
| SAP | 50 mg/l |
| Perfume, preservatives | q.s. |
| Water, completely demineralized | to 100.00 |
| pH: | to 5.5–6.0 |

EXAMPLE 8

Hair rinse

| | % by wt. |
|---|---|
| Cocoamidopropylbetaine | 5.00 |
| Cetyl alcohol | 2.00 |
| Propylene glycol | 2.00 |
| SAP | 100 mg/l |
| Perfume, preservatives | q.s. |
| Water, completely demineralized | to 100.00 |
| pH: | to 5.5–6.0 |

EXAMPLE 9

Foot cream

| | % by wt. |
|---|---|
| Soluan 5 | 2.00 |
| Methyl salicylate | 5.00 |
| Caprylic/capric triglyceride | 10.00 |
| Stearic acid | 5.00 |
| Cetyl alcohol | 1.00 |
| Glycerol | 2.00 |
| Dimethicone | 1.00 |
| Carbopol 984 | 0.50 |
| Triethanolamine | 1.50 |
| SAP | 100 mg/l |
| Perfume, preservatives | q.s. |
| Water, completely demineralized | to 100.00 |
| pH: | to 5.5–6.0 |

EXAMPLE 10

Deodorant pump spray

| | % by wt. |
|---|---|
| PEG 40-hydrogenated castor oil | 2.00 |
| Glycerol | 1.00 |
| SAP | 50 mg/l |
| Perfume, preservatives | q.s. |
| Water, completely demineralized | to 100.00 |
| pH: | to 5.5–6.0 |

What is claimed is:

1. A peptide which is a monomer, homodimer, heterodimer, homotrimer, heterotrimer, homotetramer or heterotetramer, said peptide comprising an amino acid sequence as said monomer or as a homomonomer or heteromonomer of said homodimer, heterodimer, homotrimer, heterotrimer, homotetramer or heterotetramer, said amino acid sequence being selected from:

A) the amino acid sequence:

```
Gly Ile Gly Asp Pro Val Thr Cys Leu Lys
 1               5                  10

Ser Gly Ala Ile Cys His Pro Val Phe Cys
                 15                  20

Pro Arg Arg Tyr Lys Gln Ile Gly Thr Cys
                 25                  30

Gly Leu Pro Gly Thr Thr Cys Cys Lys Lys Pro
                 35                  40
``` which has been designated at SEQ ID NO.:2

B) an amino acid sequence identical to the amino acid sequence in A), but modified in at least one of the following respects:
   i) 1–5 amino acids have been deleted;
   ii) 1–5 amino acids have been replaced by 1–5 different amino acids; or
   iii) 1–5 amino acids have been inserted;

C) an amino acid sequence identical to the amino acid sequence in A), but modified in at least one of the following respects:
   i) 1–17 amino acids have been deleted from the C-terminus;
   ii) 1–17 amino acids have been inserted at the C-terminus;
   iii) 1–17 amino acids have been deleted from the N-terminus; or
   iv) 1–17 amino acids have been inserted at the N-terminus; and D) if said peptide is a peptide or protein having a molecular weight between 10 and 100 kDaltons, an amino acid sequence comprising at least one of the amino acid sequences in A), B) or C) once or recurring several times.

2. A peptide according to claim 1, which is a monomer, homodimer, heterodimer, homotrimer, heterotrimer, homotetramer or heterotetramer, said peptide comprising an amino acid sequence as said monomer or as a homomonomer or heteromonomer of said homodimer, heterodimer, homotrimer, heterotrimer, homotetramer or heterotetramer, said amino acid sequence being the amino acid sequence:

```
Gly Ile Gly Asp Pro Val Thr Cys Leu Lys
 1               5                  10

Ser Gly Ala Ile Cys His Pro Val Phe Cys
                 15                  20

Pro Arg Arg Tyr Lys Gln Ile Gly Thr Cys
                 25                  30

Gly Leu Pro Gly Thr Thr Cys Cys Lys Lys Pro
                 35                  40
``` which has been designed SEQ ID NO.:2.

3. A cosmetic or pharmaceutical composition comprising an antimicrobially, antimycotically or antivirally effective amount of at least one peptide according to either one of claims 7–8.

4. The cosmetic or pharmaceutical composition according to claim 3, which comprises 0.0005–50% by weight of said peptide based on the total weight of the composition.

5. The cosmetic or pharmaceutical composition according to claim 4, which comprises 0.01–20% by weight of said peptide based on the total weight of the composition.

6. The cosmetic or pharmaceutical composition according to claim 5, which comprises 0.02–5% by weight of said peptide based on the total weight of the composition.

7. The cosmetic or pharmaceutical composition according to claim 6, which comprises 0.5–3% by weight of said peptide based on the total weight of the composition.

8. A method of combating bacteria, mycota and/or viruses, said method comprising topically applying to a person an effective amount therefor of the cosmetic or pharmaceutical composition according to claim 3.

* * * * *

SEQUENCE LISTING

```
<160> NUMBER OF SEQ ID NOS: 2

<210> SEQ ID NO: 1
<211> LENGTH: 40
<212> TYPE: PRT
<213> ORGANISM: Human
<220> FEATURE:
<223> OTHER INFORMATION: Xaa can be selected at will from the group
      consisting of the essential and non-essential amino acids.

<400> SEQUENCE: 1

Gly Ile Gly Asp Pro Val Thr Xaa Leu Lys Ser Gly Ala Ile Xaa His
 1               5                  10                  15

Pro Val Phe Xaa Pro Arg Arg Tyr Lys Gln Ile Gly Gly Xaa Gly Leu
                20                  25                  30

Pro Xaa Thr Lys Xaa Xaa Xaa Xaa
            35                  40
```

```
<210> SEQ ID NO: 2
<211> LENGTH: 41
<212> TYPE: PRT
<213> ORGANISM: Human
<220> FEATURE:
<223> OTHER INFORMATION: Xaa can be selected at will from the group
      consisting of the essential and non-essential amino acids.

<400> SEQUENCE: 2

Gly Ile Gly Asp Pro Val Thr Cys Leu Lys Ser Gly Ala Ile Cys His
 1               5                  10                  15

Pro Val Phe Cys Pro Arg Arg Tyr Lys Gln Ile Gly Thr Cys Gly Leu
             20                  25                  30

Pro Gly Thr Thr Cys Cys Lys Lys Pro
         35                  40
```